(12) United States Patent
Rogers et al.

(10) Patent No.: US 6,840,941 B2
(45) Date of Patent: Jan. 11, 2005

(54) VERTEBRAL ENDPLATE CHISEL

(75) Inventors: Christopher Rogers, Taunton, MA (US); John Daniel Malone, Cumberland, RI (US)

(73) Assignee: Depuy Acromed, Inc., Raynham, MA (US)

( * ) Notice: Subject to any disclaimer, the term of this patent is extended or adjusted under 35 U.S.C. 154(b) by 125 days.

(21) Appl. No.: 09/998,972

(22) Filed: Oct. 31, 2001

(65) Prior Publication Data

US 2003/0083664 A1 May 1, 2003

(51) Int. Cl.[7] .............................................. A61B 17/16
(52) U.S. Cl. ......................................... 606/79; 606/84
(58) Field of Search ............................ 606/61, 79, 84, 606/86, 99, 167, 184

(56) References Cited

U.S. PATENT DOCUMENTS

| | | |
|---|---|---|
| 4,586,496 A | 5/1986 | Keller |
| 4,697,586 A | 10/1987 | Gazale |
| 4,736,738 A | 4/1988 | Lipovsek et al. |
| 4,881,534 A | 11/1989 | Uhl et al. |
| 5,250,050 A | 10/1993 | Poggie et al. |
| 5,423,825 A | 6/1995 | Levine |
| 5,562,736 A | 10/1996 | Ray et al. |
| 5,571,109 A | 11/1996 | Bertagnoli |
| 5,649,945 A | 7/1997 | Ray et al. |
| 5,722,977 A | 3/1998 | Wilhemy |
| 5,803,904 A | 9/1998 | Mehdizadeh |
| 5,961,522 A | 10/1999 | Mehzdizadeh |
| 6,042,582 A | 3/2000 | Ray |
| 6,063,088 A | 5/2000 | Winslow |
| 6,096,038 A | 8/2000 | Michelson |
| 6,126,664 A | 10/2000 | Troxell et al. |
| 6,174,311 B1 | 1/2001 | Branch et al. |
| 6,200,322 B1 | 3/2001 | Branch et al. |
| 6,224,607 B1 | 5/2001 | Michelson |
| 6,228,022 B1 | 5/2001 | Friesem |
| 6,241,729 B1 | 6/2001 | Estes et al. |
| 6,241,733 B1 * | 6/2001 | Nicholson et al. ............ 606/84 |
| 6,261,293 B1 | 7/2001 | Nicholson et al. |
| 6,436,101 B1 * | 8/2002 | Hamada ....................... 606/85 |
| 6,599,291 B1 * | 7/2003 | Foley et al. .................. 606/79 |
| 6,610,065 B1 * | 8/2003 | Branch et al. ................ 606/84 |
| 6,641,582 B1 | 11/2003 | Hanson et al. |
| 2001/0010001 A1 | 7/2001 | Michelson |
| 2001/0010002 A1 | 7/2001 | Michelson |

FOREIGN PATENT DOCUMENTS

| | | | |
|---|---|---|---|
| JP | 126647 | * | 5/1996 |
| JP | 210316 | * | 8/2000 |

OTHER PUBLICATIONS

John W. Brantigan, *Lumbar I/F Cage with VSP Spinal System Surgical Technique*, DePuy Acromed, Raynham, MA 1999.

John W. Brantigan et al., *Posterior Lumbar Interbody Fusion Technique using the Variable Screw Placement Spinal Fixation System*, SPINE: State of the Art Reviews, Jan. 1992, vol. 6, No. 1, Handley & Belfus, Inc., Philadelphia, PA.

John W. Brantigan, *Lumbar I/F Cage Implants & Instruments Product Catalog*, DePuy AcroMed, Raynham, MA 1999.

John W. Brantigan, *Brantigan I/F Cage Implant for PLIF Technique Manual*, Apr. 16, 1990.

John W. Brantigan, *Brantigan I/F Cage for PLIF Surgical Technique*, AcroMed, Apr. 24, 1991.

(List continued on next page.)

*Primary Examiner*—Ralph A. Lewis

(57) ABSTRACT

A vertebral endplate chisel having upper and lower shaving portions, and a non-cutting guide integrally connected to and extending between the shaving portions and adapted to center the chisel within the disc space so that equal amounts of bone are removed from each endplate by the shaving portions as the chisel moves through the disc space.

42 Claims, 8 Drawing Sheets

OTHER PUBLICATIONS

Paul H. Harmon, *Anterior Excision and Vertebral Body Fusion Operation for the Intervertebral Disk Syndromes of the Lower Spine: three to five year results in 244 Cases*, Clinical Orthopaedics and Related Research, vol. 26, pp. 107–127, 1963, J.B. Lippincott Company, Philadelphia and Montreal.

Paul H. Harmon, *Congenital and Acquired Anatomic Variations, Including Degenerative Changes of the Lower Lumbar Spine; Role in Production of Painful Back and Lower Extremity Syndromes*, Clinical Orthopaedics and Related Research, vol. 44, pp. 171–186, Jan.–Feb. 1966, J.B. Lippincott Company, Philadelphia and Montreal.

Paul H. Harmon, *Indications for Spinal Fusion in Lumbar Diskopathy, Instability and Arthrosis, Part 1*, Clinical Orthopaedics and Related Research, vol. 34, pp. 73–91, May–Jun. 1964, J.B. Lippincott Company, Philadelphia and Montreal.

Paul H. Harmon, *Indications for Spinal Fusion in Lumbar Diskopathy, Instability and Arthrosis, Part 2*, Clinical Orthopaedics and Related Research, vol. 34, pp. 92–107, May–Jun. 1964, J.B. Lippincott Company, Philadelphia and Montreal.

Paul H. Harmon, *A Simplified Surgical Technic for Anterior Lumbar Diskectomy and Fusion; Avoidance of Complications; Anatomy of the Retroperitoneal Veins*, Clinical Orthopaedics and Related Research, vol. 37, pp. 130–144, Nov.–Dec. 1964 J.B. Lippincott Company, Philadelphia and Montreal.

Paul H. Harmon et al., *Correlation of Multiple Objective Diagnostic Methods in Lower Lumbar Disk Disease*, Clinical Orthopaedics and Related Research, vol. 28, pp. 132–151, 1963, J.B. Lippincott Company, Philadelphia and Montreal.

A. H. Mackenzie, *Steel Ball Arthroplasty of Lumbar Intervertebral Discs–a Preliminary Report*, The Journal Of Bone and Joint Surgery, British Volume, vol. 54–B, p. 766, Nov. 1972, Messrs E. & S. Livingstone.

Alvin H. Mackenzie, MD, *Fernstrom Intervertebral Disc Arthroplasty: A Long–term Evaluation*, Orthopaedics International Edition, Jul./Aug. 1995 Vol 3 No 4, pp. 313–324.

George W. Bagby, MD, MS, *Arthrodesis by the Distraction–Compression Method using a Stainless Steel Implant*, Orthopedics, Jun. 1988 Vol 11/No 6, pp. 931–934.

Paul M. Lin, MD, FACS, *Posterior Lumbar Interbody Fusion Technique: Complications and Pitfalls*, Clinical Orthopaedics and Related Research, No. 193, Mar. 1985, pp. 90–102.

John C. Collis, MD, *Total Disc Replacement: A Modified Posterior Lumbar Interbody Fusion Report of 750 Cases*, Clinical Orthopaedics and Related Research, No. 193, Mar. 1985, pp. 64–67.

Gabriel W. C. MA, MD, FACS, *Posterior Lumbar Interbody Fusion with Specialized Instruments*, Clinical Orthopaedics and Related Research, No. 193, Mar. 1985, pp. 57–63.

Ralph B. Cloward, MD, *Posterior Lumbar Interbody Fusion Updated*, Clinical Orthopaedics and Related Research, No. 193, Mar. 1985, pp. 16–19.

Paul M. Lin, MD et al., *Posterior Lumbar Interbody Fusion*, Clinical Orthopaedics and Related Research, No. 180, Nov. 1983, pp. 154–168.

Ralph B. Cloward, MD, *Spondylolisthesis: Treatment by Laminectomy and Posterior Interbody Fusion Review of 100 Cases*, Clinical Orthopaedics and Related Research, No. 154, Jan.–Feb. 1981, pp. 74–82.

Paul M. Lin, MD, *A Technical Modification of Cloward's Posterior Lumbar Interbody Fusion*, Neurosurgery, vol. 1, No. 2, 1977, pp. 118–124.

ULF Fernstrom, *Arthroplasty with Intercorporal Endoprosthesis in Herniated Disc and in Painful Disc*, Acta Chirurgica Scandinavica, Supplement 357, pp. 154–159, Stockholm 1966.

ULF Fernstrom, *Ruptured Lumbar Discs Causing Abdominal Pain*, Acta Chirurgica Scandinavica, Supplement 357, pp. 160–161, Stockholm 1966.

* cited by examiner

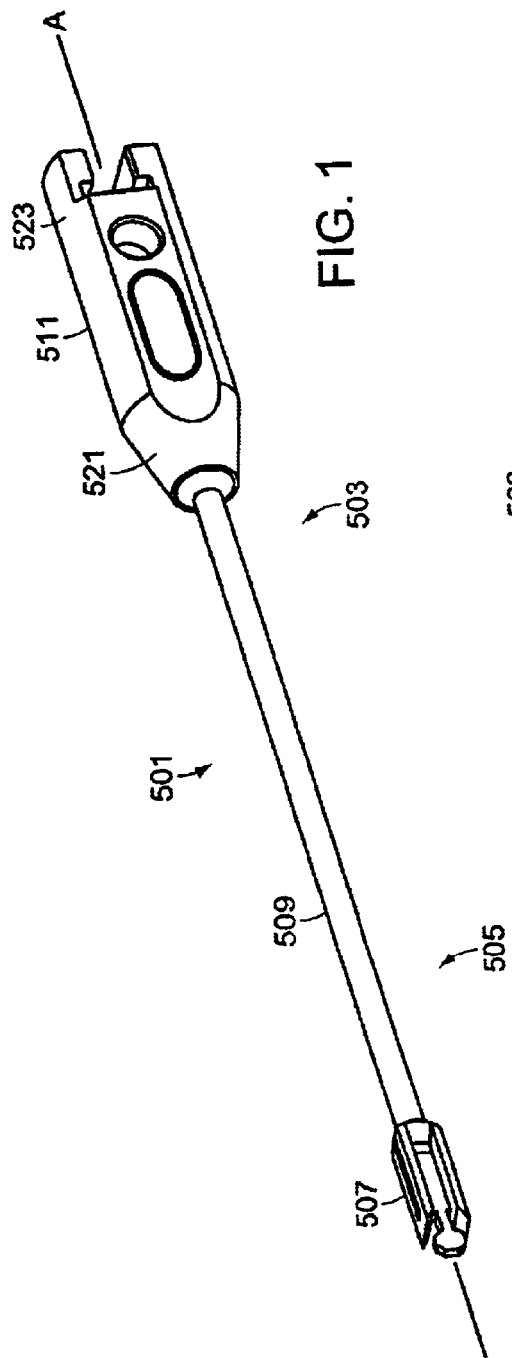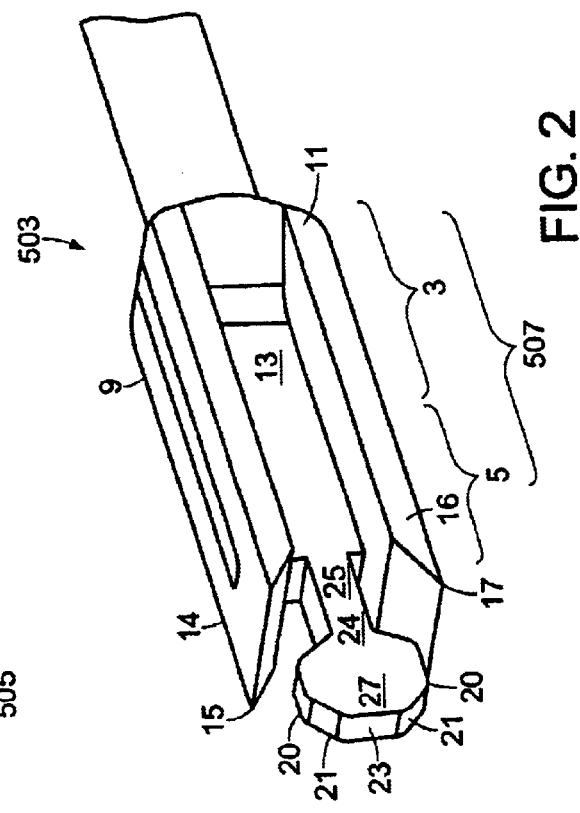
FIG. 1
FIG. 2

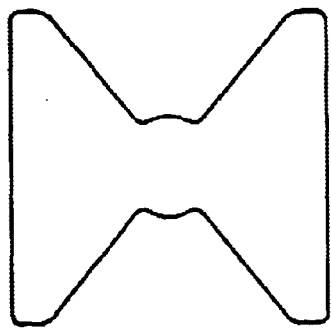
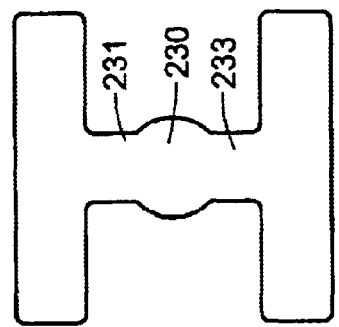
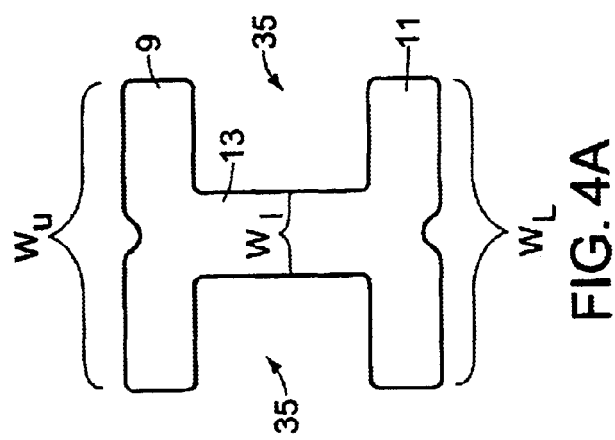
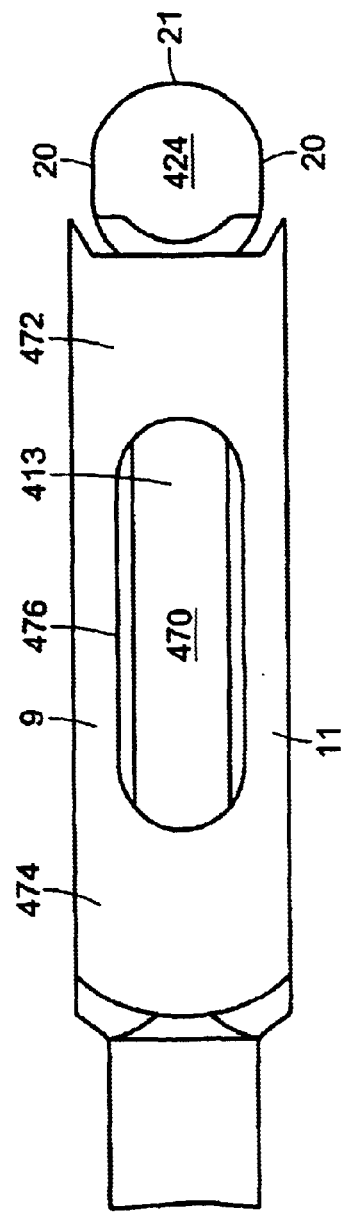
FIG. 4C
FIG. 4B
FIG. 4A
FIG. 5

VERTEBRAL ENDPLATE CHISEL

BACKGROUND OF THE INVENTION

The basic goal of a typical Posterior Lumbar Interbody Fusion ("PLIF") procedure is to remove a problematic disc, and insert a prosthetic fusion device (such as a cage or a mesh) into the empty disk space created by removal of the natural disc. However, the pathophysiology of an intervertebral disc is such that the disc space in which the disc sits is typically collapsed (e.g., 30–50% of the time) prior to disc removal. Once the natural disc is removed (but prior to implant insertion), the annulus and soft tissue surrounding the disk space tend to force the adjacent vertebrae to come even closer together, thereby increasing the extent of disk space collapse. Since one goal of the surgery is to restore the patient's anatomic disc space to the extent possible, there is a need to spread apart these collapsed vertebrae. In one conventional PLIF procedure, a flat Spreader (which resembles a butter knife) is inserted with a horizontal disposition into the collapsed disk space and then rotated 90 degrees to vertically distract the adjacent vertebrae and restore the patient's physiologic disc space. The distracted endplates are essentially parallel to each other after the Spreader is rotated.

In addition, it is further desirable that the implanted device be secure within the disk space. However, since the geometry of the disk space varies from patient to patient, and the implants are typically manufactured in only a few shapes, the implants do not typically fit congruently into the distracted disk space. Accordingly, in one conventional PLIF procedure, congruence between rectangular implant shapes and the distracted disc space height is achieved by forming rectangular channels of known dimension in the adjacent endplates.

However, the current PLIF procedure for forming substantially rectangular channels in the endplates is a time-consuming three-step process. After the full discectomy and careful distraction of the disk space by the Spreaders described above, the surgeon must first insert a Reamer into the disk space and rotate it to create rounded grooves in both the superior and inferior endplates. In a second step, the surgeon then must insert the leading edge of a Pilot Broach into the disc space and axially impacts it to create a rectangular channel on the posterior side of the endplates. In the third step, the surgeon inserts a Finish Broach into the disc space and axially impact it to complete the anterior portion of the rectangular channel. Further details of the three-step Reamer—Pilot Broach—Finish Broach procedure and conventional instrument shapes can be found in a Brantigan et al. "Posterior Lumbar Interbody Fusion Techniques Using the Variable Screw Placement Spinal Fixation System" 6(1) in Spine: State of the Art Reviews. January 1992, pp. 175–200.

The Pilot Broach noted above has a body portion, a rectangular shaver portion extending distally from the body portion, and a cylindrical spreader portion extending from the shaver. The larger axial silhouette of the shaver portion relative to the cylindrical spreader portion defines shaving corners. The leading edge of the cylindrical spreader portion has a flat. Cylindrical spreader portion also includes an upper surface and a lower surface each of which bear upon the endplates. A crown is situated at the proximal end of the Pilot Broach and is used to engage a complimentary engagement connection.

Although the PLIF procedure using the Pilot Broach has been popular with surgeons, there have also been requests for improved instrumentation. In particular, surgeons have requested a quicker, easier 1-step method of preparing the rectangular channel in the endplates prior to implantation.

FIGS. 11b and 11c of U.S. Pat. No. 6,096,038 ("Michelson") discloses a combined distractor-cutter having a distracting portion (102 in FIG. 11b and 260 in FIG. 11c) and a rotary shaving portion (270 in FIG. 11b and 250 in FIG. 11c). The distracting portion distracts the vertebral bodies while the rotary cutting portion prepares a bore shaped for the insertion of the threaded circular fusion cage.

Since each of these devices uses a rotary cutting device to prepare the endplates, the channels formed thereby are not substantially rectangular. In addition, cannulated technology (which protects the internal organs from the rotary cutting devices) is often needed when drilling devices are used, thereby increasing the complexity of the procedure.

FIGS. 25 and 25a–d of U.S. Pat. No. 6,174,311 ("Branch") disclose a chisel having i) distracting portions 272, 273 for centering the chisel between the vertebrae and ii) upper and lower shavers 268, 270 for forming a rectangular channel in the distracted vertebrae. Arms 267 and 269 define a cavity 276 for receipt of bone chips and shaving debris. FIGS. 37a–c and 38 of Branch disclose a second chisel substantially similar to the chisel of FIG. 25.

One weakness of the Branch chisel lies in the disposition of both arms 267,269 and non-cutting edges 272, 273 at the lateral edges of the device. Because these arms and edges are disposed laterally, their effective widths essentially equal the entire width of the cutting edges, and thereby interrupt the surgeon's sightlines into the disk space.

U.S. Pat. No. 5,722,977 ("Wilhelmy") discloses a combination osteotome and spacer guide. In use, as in FIG. 18, the spacer guide 8 is first inserted into the disc space 9. Next, the hollow osteotome 9 is slid over the outer dimension of the spacer guide 8 to its appropriate position. Lastly, driving head 49 of the osteotome is impacted by a mallet to drive the osteotome over the guide and into the vertebral bodies, and to cut and remove the desired amounts of bone.

One weakness of the Wilhelmy design lies in its need to slide the osteotome over the spacer guide in order to form the rectangular channel. Such sliding requires the maintence of close tolerances between the outer surface of the guide and the inner surface of the osetotome. This close tolerance may degrade with continued use. In addition, Wilhelmy teaches using separate osteotome and spacer guide instruments, thereby increasing complexity and cost. Another weakness of the Wilhelmy design lies in the relatively large width of the spacer. Since the width of the spacer must essentially equal the width of the osteotome to provide accurate cutting, the width of the spacer guide must be as large as possible. Accordingly, the surgeon's sightlines are interrupted by the device.

U.S. Pat. No. 4,697,586 ("Gazelle I") discloses a chisel having a spreader portion and a chisel configured to slide over the spreader. The surgeon using the Gazelle I device first inserts the spreader into the intervertebral space. Next, the chisel portion of the device is slid along the outer surface of the spreader and its shaving portions cut rectangular channels into the endplates.

A publicly used device ("Gazelle II") is somewhat similar to the Gazelle I device. Its main difference with Gazelle I is that the spreader of the Gazelle II device is rotatable. The surgeon using the Gazelle II device inserts the spreader into the intervertebral space and then rotates it 90 degrees to distract the disc space. Next, the chisel portion of the device is slid along the outer surface of the rotated spreader and its shaving portions cut rectangular channels into the endplates.

Like Wilhelmy, the Gazelle I and II devices require sliding the shaving portions over the distractor portion. In addition, the box nature of the chisel obscures sightlines. Lastly, the spreader has a height to width ratio of about 3:2, and so is is not relatively thin.

U.S. Pat. No. 4,736,738 ("Lipovsek") discloses a shaving instrument for performing posterior lumbar interbody fusion, the instrument comprising a shaft adapted to be inserted into the intervertebral space and a chisel adapted to be slidably received within the shaft.

In sum, prior art procedures and devices used for endplate preparation suffer from:
 a) the need to use multiple devices in multiple steps;
 b) the need to slide a chisel over or through a spacer guide; and
 c) the interruption of surgeon sightlines into the disc space.

SUMMARY OF THE INVENTION

In accordance with the present invention, there is provided a vertebral endplate chisel comprising:
 a) a base having upper and lower portions, and proximal and distal portions,
 b) an upper shaving portion extending distally from the upper base portion,
 c) a lower shaving portion extending distally from the lower base portion, the upper and lower shaving portions being disposed substantially parallel to each other and each having a width, and
 d) a guide integrally connected to and extending distally from the base, the guide located between the shaving portions and having a width,
wherein the width of the guide is no more than 95% of the width of the upper shaving portion.

This device allows preparation of the rectangular channel in one step. After a full discectomy has been performed and careful distraction of the disc space has been achieved, the surgeon places the inventive device against the posterior lip of the endplate, carefully aligns the instrument, and lightly impacts the device into the disc space to create the complete rectangular channel.

Since the width of the guide of the inventive device is less than the width of the upper shaving portion, the surgeon's sightlines into the disk space are not completely interrupted by the width of the guide as with the Branch device.

Since the shaving portions of the inventive device define substantially parallel planes (i.e., the shaving portion is not rotary), not only is a rectangular channel formed but also there is no need to use cannulated technology as with the Michelson device.

Lastly, since the guide of the inventive device is integrally connected to the base, shaving is performed by simply precisely locating the shaving portions at the desired depth of the vertebral surface and tapping the proximal end of the device with a hammer, and so does not require sliding the shaver over the guide as with the Gazelle and Wilhelmy devices.

DESCRIPTION OF THE FIGURES

FIG. 1 discloses a first perspective view of a first embodiment of the inventive device.

FIG. 2 discloses a perspective view of a distal portion of the first embodiment of the inventive device.

FIGS. 4a–4c disclose cross-sectional views through the base portion of three devices of the present invention.

FIG. 5 discloses a side view of a second embodiment of the inventive device.

DETAILED DESCRIPTION OF THE INVENTION

Figure 3:
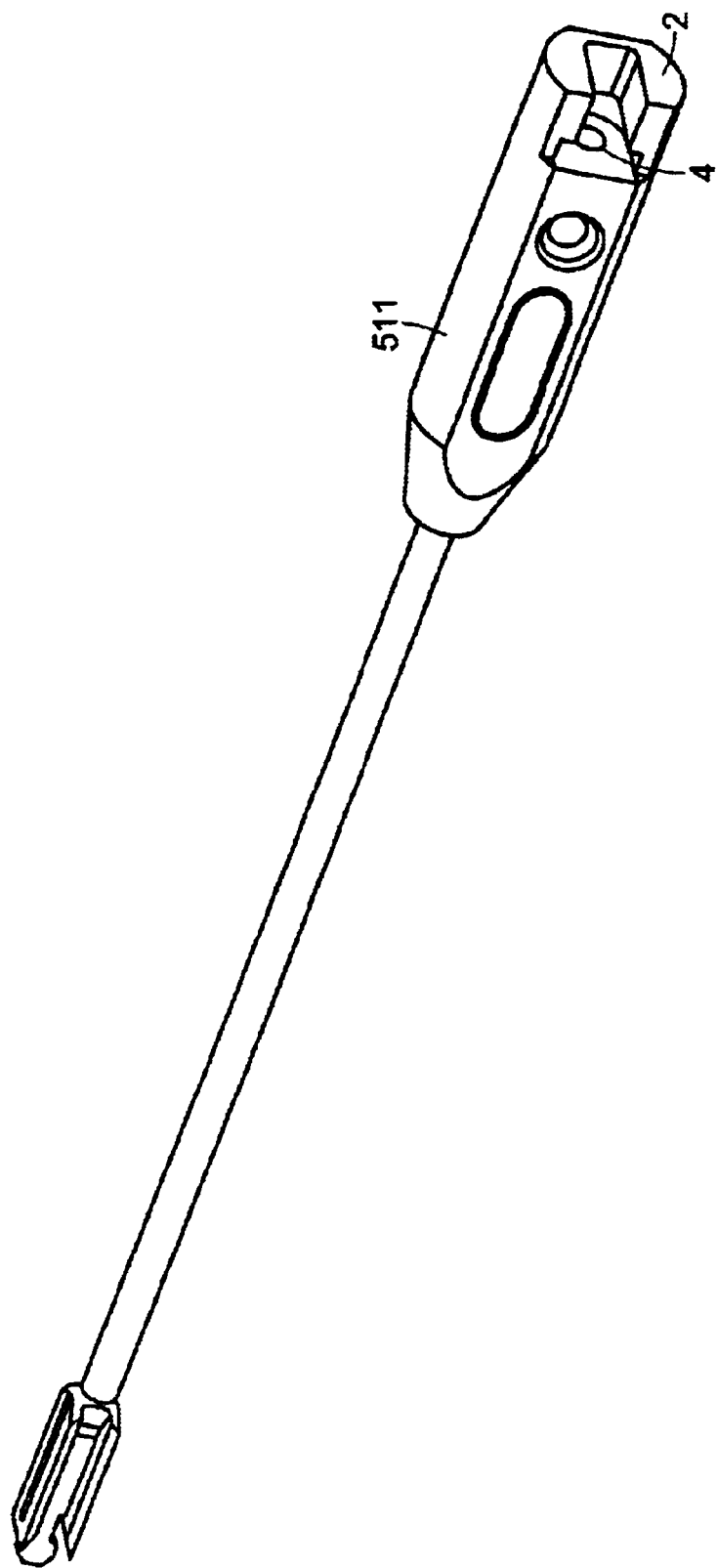
FIG. 3 discloses a second perspective view of the first embodiment of the inventive device.

Now referring to FIG. 1, the box chisel device 501 as a whole preferably has a proximal portion 503 and a distal portion 505. Preferably, the device includes distal base portion 507, an intermedite longitudinal portion 509 defining longitundinal axis A, and a handle portion 511 located proximal to the proximal portion of the base. The handle comprises a distal perimeter 521 and a proximal perimeter 523, the distal perimeter being smaller than the proximal perimeter.

Now referring to FIG. 2, base portion 507 of the chisel may be shaped to have its own proximal portion 3 and distal portion 5. In some embodiments, as in FIG. 3, the handle portion 511 at the proximal end of the device may terminate in a substantially flat surface 2 which provides an impact surface for a mallet or hammer. The proximal end may also be shaped without such a handle but with an extraction means so as to enable its connection to an extraction device. Preferably, the handle portion 511 comprises a female portion 4, as in FIG. 3, or a male portion, for that purpose.

Now referring to cross-sectional FIG. 4a, a cross-section of the base 507 includes upper portion 9, lower portion 11, and intermediate portion 13. In some embodiments, as in FIG. 5, at least a portion of each of the upper 9, intermediate 11 and lower 13 portions of the base may have the same width W so that the shape of at least a portion 474 of the base may have a substantially blocky shape. In this embodiment, the proximal portion 474 of the base has a blocky shape.

Referring back to FIG. 4a, in some embodiments, the base is shaped so as to provide pathways for the removal of bone debris from the area around the shaving portions. In some embodiments, the intermediate portion 13 has a width $W_I$ which is thinner than the widths $W_U$ and $W_L$ of the adjacent upper 9 and lower 11 portions, thereby providing flutes 35 for removal of the debris.

Therefore, in some embodiments, as in FIG. 4a, the base of the box chisel has an integral I-beam-like shape comprising:
 i) an intermediate portion 13,
 ii) an upper portion 9 integrally connected to the intermediate portion, and iii) a lower portion 11 integrally connected to the intermediate portion, wherein each of the intermediate, upper and lower portions has a width, and wherein the width of each of the upper and lower portions is greater than the width of the intermediate portion.

The I-beam-like shape includes the conventional I-beam shape, as shown in FIG. 4a, a bulging I-beam shape, as in FIG. 4b, and a bow-tie shape, as in FIG. 4c.

The I-beam-like shape is advantageous because it minimizes the amount of material needed in the base section of the device, thereby maximizing debris pathway cross-section but without compromising the strength of the base section.

In some embodiments, upper 9 and lower 11 base portions do not contact the inner portion 470 of the intermediate portion, as in FIG. 5, so that pathways for debris are formed between the inner surfaces of the upper and lower portions and the outer surface of the inner portion 470. In such embodiments, the upper and lower base portions may be integrally connected by virtue of lateral intermediate portions 472, Holes 476 may be provided in lateral portions 472 in order to assist debris removal.

Figure 6:
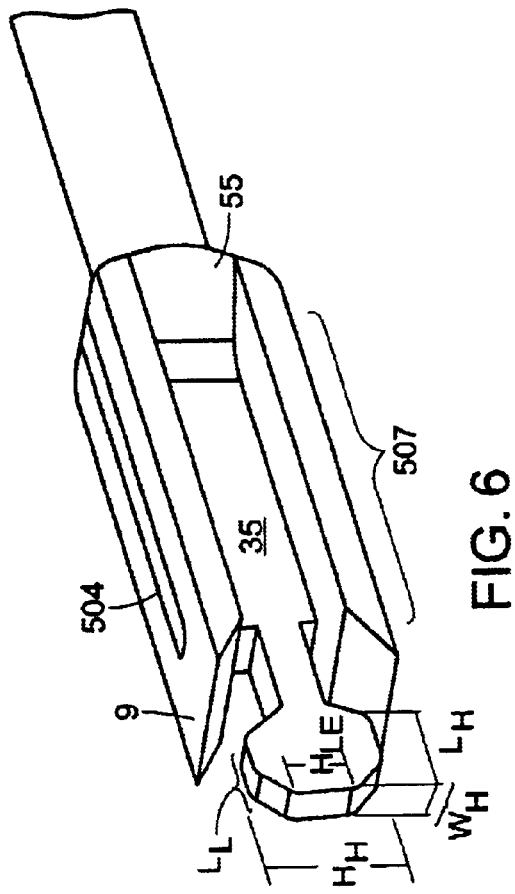
FIG. 6 discloses another perspective view of a distal portion of the first embodiment of the inventive device.

Now referring to FIG. 6, in some embodiments, in the proximal end of the I-beam-like portion of the base, the width of the intermediate section 55 widens towards the proximal end. This tapering directs the bone debris out of the pathway and prevents clogging.

Figure 7:
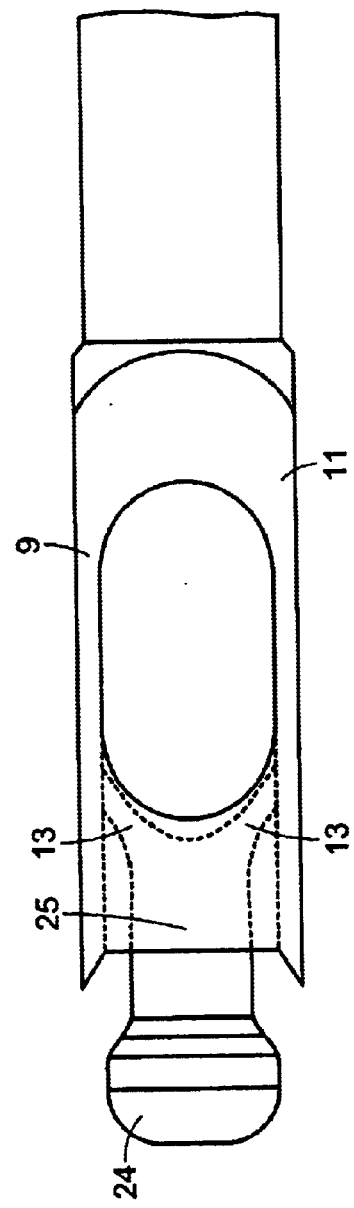
FIG. 7 discloses a side view of a distal portion of a third embodiment of the inventive device.

In other embodiments, as in FIG. 7, the intermediate portion 13 of the base extends from both the upper 9 and lower 11 base portions, and transitions into a neck 25 of guide 24.

Figure 8:
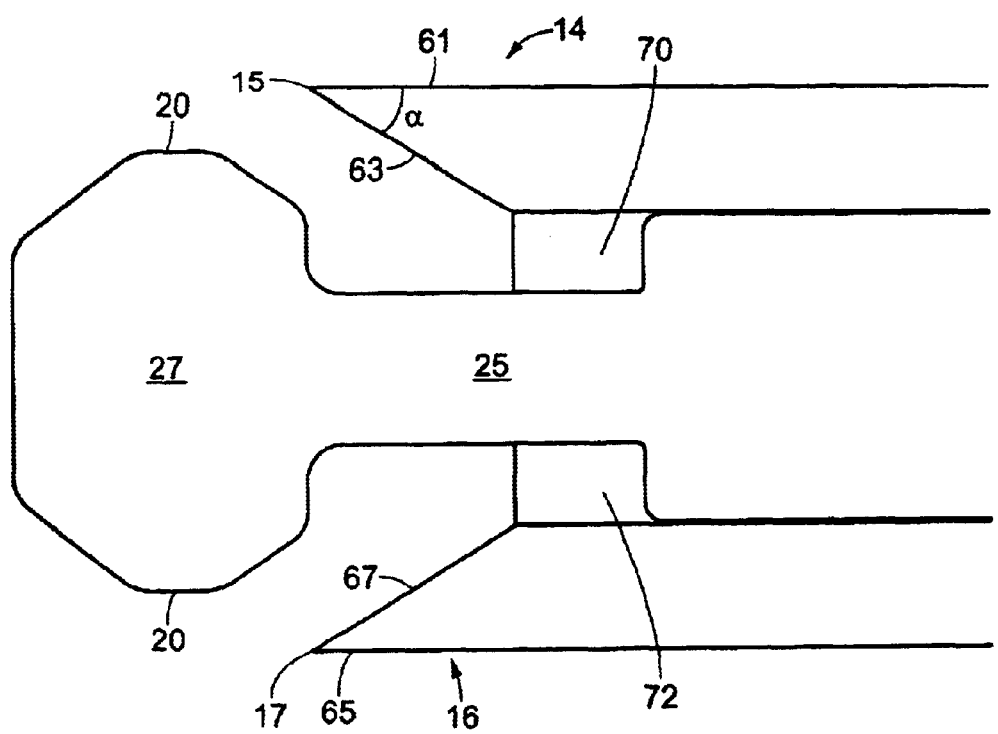
FIG. 8 discloses a side view of a distal portion of the first embodiment of the inventive device.

Now referring to FIG. 8, the upper and lower shaving portions should be oriented substantially parallel to one another in order to create a substantially rectangular channel between the vertebral endplates. Preferably, upper shaving portion 14 comprises an outer surface 61 and an inner surface 63 whose intersection forms a tip 15 having an angle α suitable for shaving endplates. Preferably, angle α is between 20 and 40 degrees. When the angle α is more than 40 degrees, the device does not produce a clean cut. When the angle α is less than 20 degrees, the tip dulls quickly. Preferably, lower shaving portion 16 comprises an outer surface 65 and an inner surface 67 whose intersection forms a tip having the same angle α as that of the upper shaving portion. When the outer surfaces 61,65 of the shaving portions are parallel, the shaved bone is directed towards the debris pathways and a rectangular channel is formed.

Still referring to FIG. 8, preferably, the head portion 27 of the guide extends further distally than the shaving portions. In this condition, the head 27 acts as a centering device which insures that the equal depth of bone is shaved from each adjacent endplate. More preferably, head 27 possesses upper and lower lands 20 which help stabilize the device as it moves through the disc space and assists in the centering function. Preferably, at least a portion of each the lands is positioned distal to the tips, 15, 17 of the shaving portions 14,16. These leading portions further stabilize the device upon its initial entry into the disc space, and prevent clogging.

Figure 9:
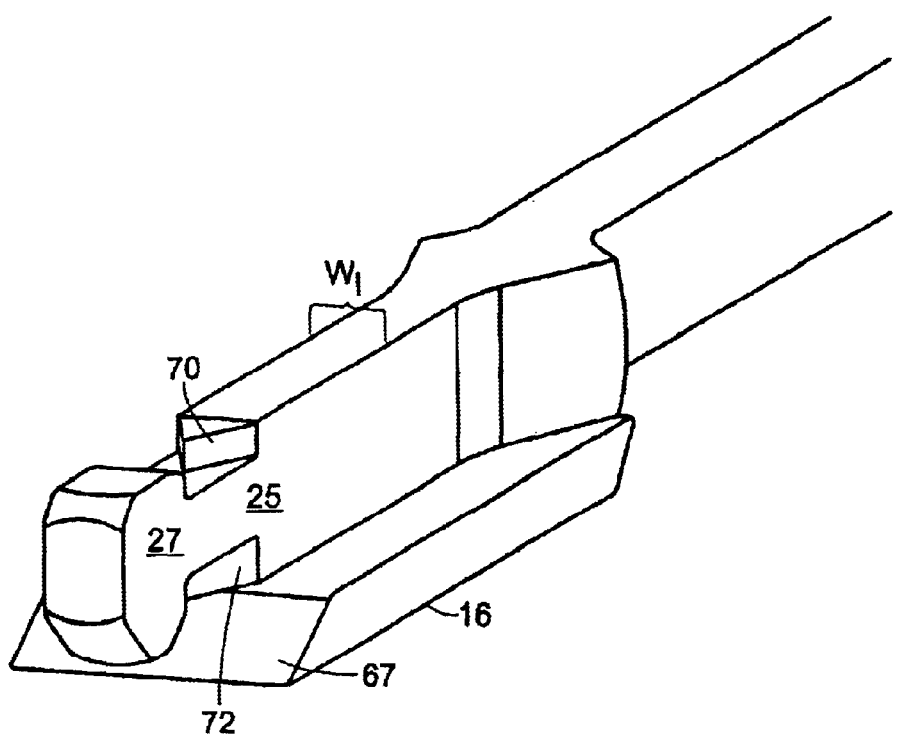
FIG. 9 discloses a perspective view of the first embodiment of the inventive device having been axially sliced.

Now referring to FIGS. 8 and 9, in some embodiments, the width of the distal end of the intermediate section narrows as it extends to form a pair of secondary orthogonal shavers 70,72. These orthogonal shavers are located between the upper and lower shaving portions 14,16 and are oriented orthogonal to the shaving portions 14,16. In one embodiment, the secondary orthogonal shavers 70,72 are located on either side of neck 25 from which the head 27 distally extends. Upon axial advance of the device, these secondary orthogonal shavers 70,72 further split the portion of the bone already shaved from the upper and lower shavers 14,16, thus preventing the bone from wedging into the device and being driven anteriorly.

Figure 10:
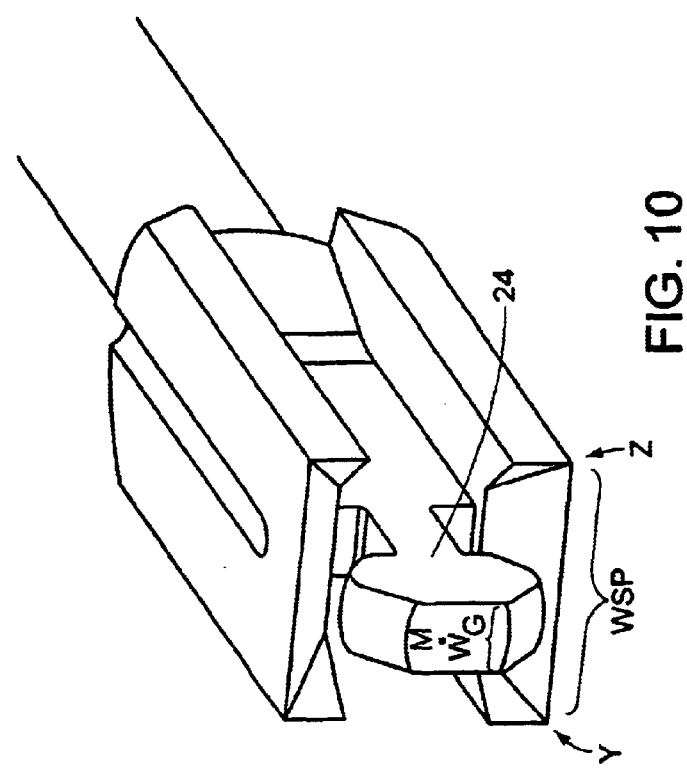
FIG. 10 discloses a perspective view of a fourth embodiment of the invention having cornered cutting tips.

Now referring to FIG. 10, the general function of the guide 24 is to insure that the device is centered within the disc space so that equal amounts of bone are removed from each endplate. When the guide is centered between the shaving portions (i.e., its midpoint M is located between the 40% and 60% of the distance from edges Y and Z), substantially equal amounts of bone are removed from each endplate.

Preferably, the guide is shaped so as to minimize interruption of the surgeon's sightlines. In some embodiments, the guide has a thin width. When the guide has such a thin width, the surgeon can more easily see the disc space. Preferably, the guide width WG is no more than 50% of the shaving portion width $W_{SP}$, more preferably no more than 25%. In some embodiments, the guide is centered between the widths of the shaving portions. When the guide is so centered, the surgeon can see the disk space as easily from one side of the device as the other.

In some embodiments, the guide is sufficiently thin and centered so that the entire guide width is located within the middle one-third of the width $W_{SP}$ of the shaving portions. More preferably, the guide is sufficiently thin and centered so that the entire guide width is located within the middle one-fifth of the width of the shaving portions.

Now referring to FIG. 2, in some embodiments, the guide 24 includes a neck portion 25 extending from the intermediate portion of the base and a head portion 27 extending from the neck. In some embodiments, as in FIG. 2, the neck is rectangularly shaped. In other embodiments, as in FIG. 11 the neck widens at an angle β as it extends from the intermediate extending portion to the head. In that embodiment, the angle β of the neck widening is substantially equal to the angle α formed by the tip of the shaving portion. In such embodiments, the bone debris pathway formed by the inner surface (e.g., inner surface 63) of the shaving portion and the relevant neck surface (e.g., surface 26) has parallel walls.

Figure 11:
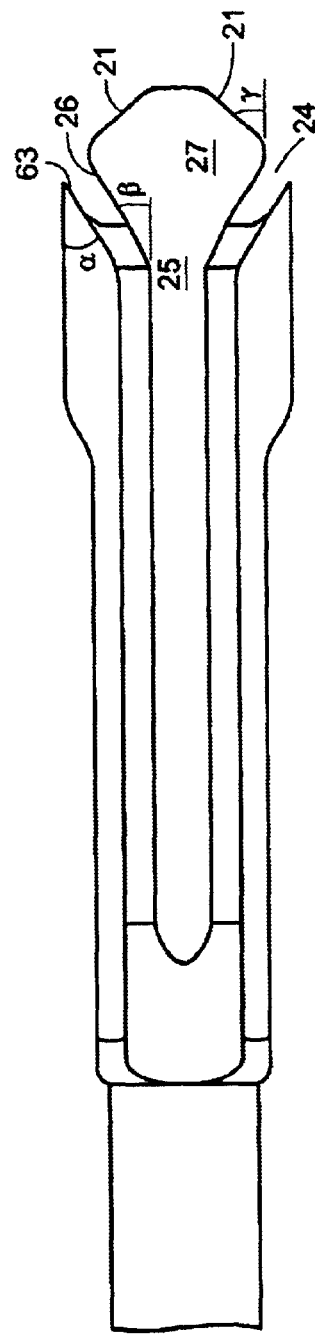
FIG. 11 discloses a side view of a fifth embodiment of the present invention.

Still referring to FIG. 11, in some embodiments, the distal section of the guide head 27 has a tapered portion 21. The tapered portion helps ease device into the distracted disc space. Preferably, the angle γ of the taper is between 30 and 60 degrees. When the angle is less than 30 degrees, the tapered portion must be very long. When the angle is more than 60 degrees, the taper is too blunt to achieve easy insertion.

In some embodiments, as in FIG. 11, the axial cross section of the head has a nipple shape. That is, the cross section consists essentially of a tapered front section having little or no land portion. In other embodiments, and now referring to FIG. 12, the axial cross section of the head has a bullet shape. That is, the cross section includes broad lands 320 and a tapered distal section 321.

Figure 13:
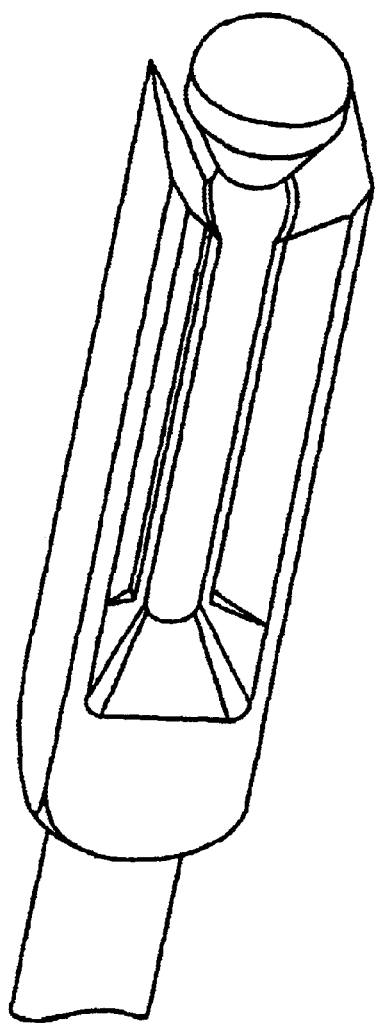
FIG. 13 discloses a perspective view of the sixth embodiment of the present invention.

Now referring to FIG. 13, in some embodiments, the radial cross-section of the head has a circular shape. Preferably, however, the radial cross section of the head has a rectangular shape having a height and a width, as in FIG. 6. Preferably, the rectangular or triangular shape is dimensioned so that the height $H_H$ is at least 5 times the width $W_H$.

Although in preferred embodiments, the device is a single integral piece, in some embodiments, the device may be modular. For example, in some embodiments having a thin, centered guide, the shaving portions may be slidable over the outer surfaces of the guide.

Preferably, the device is made from either a metal or a ceramic material, or a composite of metals and ceramics. The device should be sterilized before use in a procedure. More preferably, the device is made of stainless steel.

Also in accordance with the present invention, there is provided a vertebral endplate chisel comprising:
 a) a base having upper, lower and intermediate portions, and proximal and distal portions,
 b) no more than two shaving portions for contouring vertebral endplates, comprising:
  i) an upper shaving portion extending distally from the upper portion, and
  ii) a lower shaving portion extending distally from the lower portion,
 the upper and lower shaving portions being disposed substantially parallel to each other to define a separation distance, each shaving portion having a vertically extending portion extending toward the opposite shaving portion for a distance of between 0% and 30% of the separation distance, and
 c) a guide extending from the intermediate portion of the base.

Preferably, each vertically extending portion extends toward the opposite shaving portion for a distance of between 0% and 15% of the separation distance. More preferably, each shaving portion has substantially no vertically extending portion.

Also in accordance with the present invention, there is provided a vertebral endplate chisel comprising:
 a) a base having upper and lower portions, and proximal and distal portions,
 b) an upper shaving portion extending distally from the upper portion,
 c) a lower shaving portion extending distally from the lower portion, the upper and lower shaving portions being disposed substantially parallel to each other, and
 d) a single guide disposed between the shaving portions and extending distal to the shaving portions, and having a height and a width, wherein the height of the single guide at least b 5times greater than its width.

Also in accordance with the present invention, there is provided a vertebral endplate chisel comprising:
 a) a base having upper and lower portions extending distally therefrom,
 b) an upper shaving portion extending distally from the upper portion,
 c) a lower shaving portion extending distally from the lower portion, the upper and lower shaving portions being disposed substantially parallel to each other, and
 d) a single guide disposed between the shaving portions and extending distal to the shaving portions, and having a height and a width, wherein the width of the single guide no more than 50% of the width of the upper and lower shaving portion.

Also in accordance with the present invention, there is provided a vertebral endplate chisel comprising:
 a) a base having upper, intermediate and lower portions, and proximal and distal portions,
 b) an upper shaving portion extending distally from the upper portion,
 c) a lower shaving portion extending distally from the lower portion, the upper and lower shaving portions being disposed substantially parallel to each other,
 wherein the intermediate base portion narrows at the distal end thereof to form secondary orthogonal shavers.

Also in accordance with the present invention, there is provided a vertebral endplate chisel comprising:
 a) a base having an integral I-beam-like shape comprising:
  i) an intermediate portion,
  ii) an upper portion integrally connected to the intermediate portion, and
  iii) a lower portion integrally connected to the intermediate portion,
 wherein each of the intermediate, upper and lower portions has a width, and
 wherein the width of each of the upper and lower portions is greater than the width of the intermediate extending portion.

Example I

Now referring to FIG. 1, the Box Chisel 1 has a proximal portion 503 and a distal portion 505 formed along its longitudinal axis A. Now referring to FIG. 2, at distal portion 505 is a rectangular base 507, having upper 9, lower 11 and intermediate 13 portions. Upper and lower portions 9 and 11 terminate in distally-extending upper and lower shavers 14,16. Intermediate portion 13 terminates distally in a flat thin guide 24 having a neck portion 25 extending from the intermediate portion 13 and a head portion 27 extending from the neck 25. Head portion 27 includes upper and lower land portions 20, upper and lower tapered portions 21, and a flat leading edge 23 formed by the termination of the tapered portions prior to their convergence. Tips 15, 17 of shavers 14,16 terminate distally before the head portion 27 forms its lands 20.

The overall shape of guide 24 can be described as a pancake-like. Now referring to FIG. 6, in one exemplary sized 9×11 Box Chisel, the height $H_H$ of the head (which corresponds to the disk height) is about 9 mm; width $W_H$ of the head is about 2.5 mm, and the length $L_H$ of the head is about 5 mm. Flat leading edge 23 of the head portion 27 typically has a height $H_{LE}$ of about 5 mm. Finally, lands 20 typically have a length $L_L$ of about 1 mm.

In addition, the device of FIG. 6 contains a longitudinal groove 504 located along the upper surface of upper portion 9 of base 507. This groove reduces the stiction of the device during use.

In one method of using this device, once the disc space has been distracted by the Spreaders, the surgeon grips the Box Chisel by its proximal end and axially advances the distal end of the Box Chisel towards the distracted disc space. Since the disk space has already been distracted, tapered portions are the first portions of the tip to contact the vertebral endplates upon insertion into the disk space. If the disk space has been properly distracted, the flat leading edge portion of the tip should not contact the endplates. This initial contact between the tip tapers and the distracted endplates simply centers the Chisel Box relative to the adjacent vertebrae. Upon further axial advancement of the Box Chisel, tip contact with the endplates switches from the tapers to lands, and then finally to both lands and shavers. In this last mode, the shavers cut the endplates to form the desired channels of known dimension, such shaving being guided by the land-endplate contact.

Example II

Figure 14:
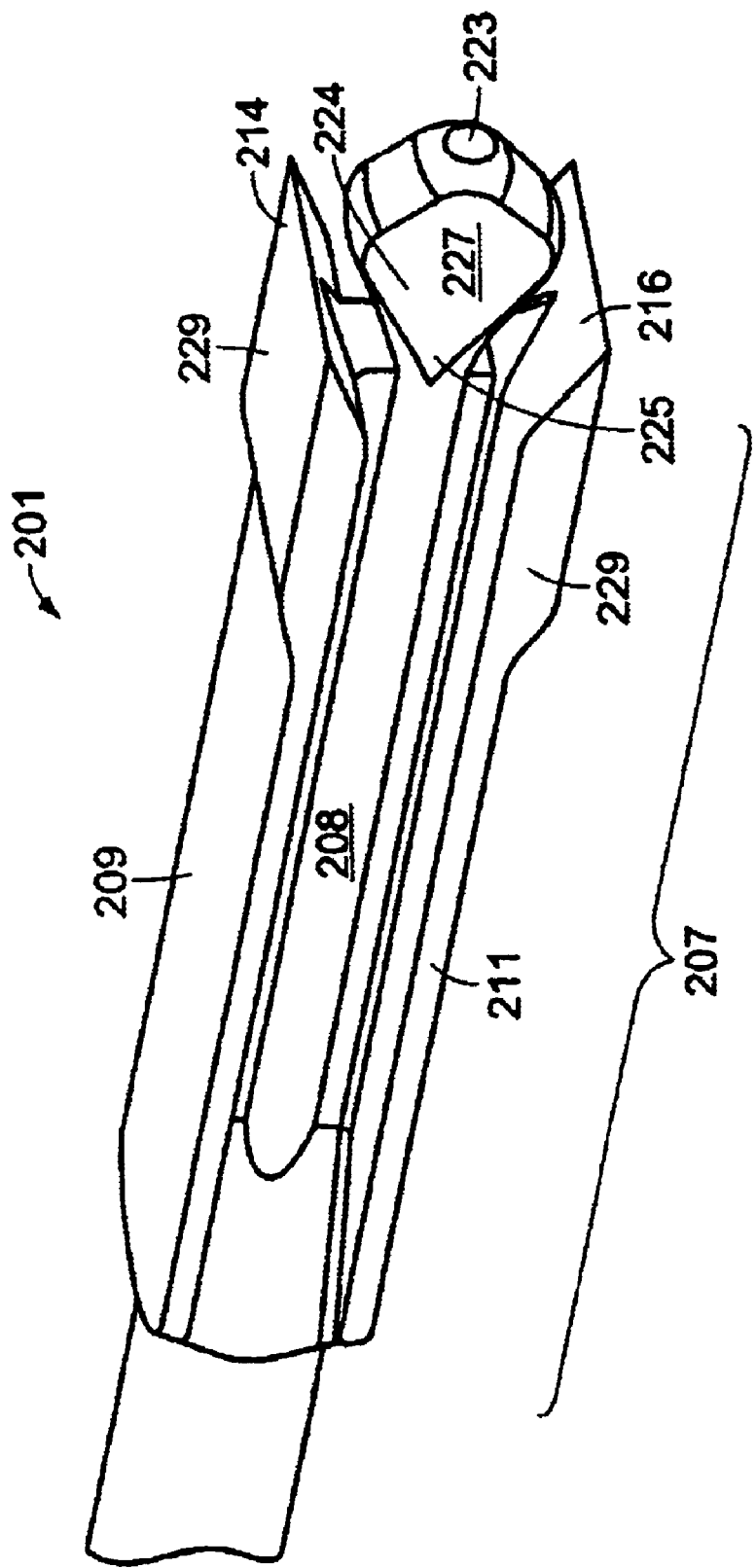
FIG. 14 discloses a perspective view of the fifth embodiment of the present invention.

In this embodiment, now referring to FIG. 14, the base 207 of the box chisel 201 has an I-Beam-like section 208.

The shavers 214,216 extend from the upper and lower base portions 209,211 and are formed by a height-increasing step 229 from the upper and lower base portions 209,211. The step reduces the stiction of the device. The guide 224 includes a i) neck portion 225 which widens as it extends distally and ii) a thin head portion 227 which has a rounded cross-section terminating in a flat leading edge 223.

Example III

Figure 12:
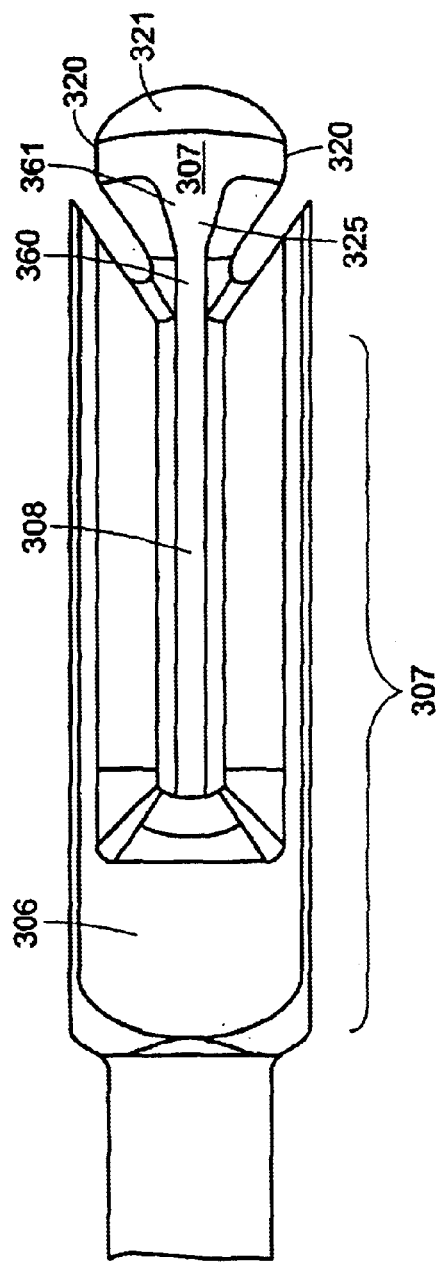
FIG. 12 discloses a side view of a sixth embodiment of the present invention.

Now referring to FIG. 12, this device includes a head 307 having lands 320 and a bullet-shaped distal section 321. The neck portion 325 of the guide includes both a rod-like section 360 and a widening section 361. The base 307 includes a substantially blocky proximal section 306 and an I-beam-like section 308.

Example IV

Now referring to FIG. 5, in this embodiment, the intermediate portion of the base comprises 413 has an inner portion 470, and lateral portions (one of which, 472 is shown). Inner portion 470 extends continuously from the proximal portion 474 of the base, while the lateral portions form the sides of a hollow box around inner portion 470. In some embodiments, the lateral portions include side holes 476. Guide 424 extends from the inner portion 470 of the intermediate base portion 413 and has a bullet shaped, radially symmetric cross section.

We claim:

1. A vertebral endplate chisel comprising:
    a) a base having upper and lower portions, and proximal and distal portions,
    b) an upper shaving portion extending distally from the upper base portion,
    c) a lower shaving portion extending distally from the lower base portion, the upper and lower shaving portions being disposed substantially parallel to each other and each having a width, and
    d) a guide integrally connected to and extending distally from the base and having a width, the guide located between the shaving portions and having a width
wherein the width of the guide is no more than 95% of the width of the upper shaving portion,
wherein the guide is a non-cutting centering device adapted to center the chisel within the disc space so that equal amounts of bone are removed from each endplate by the shaving portions as the chisel moves through the disc space.

2. The chisel of claim 1 further comprising c) a handle located proximal to the proximal portion of the base.

3. The chisel of claim 2 wherein the handle terminates in a substantially flat surface which provides an impact surface.

4. The chisel of claim 2 wherein the handle comprises a distal perimeter and a proximal perimeter, the distal perimeter being smaller than the proximal perimeter.

5. The chisel of claim 1 further comprising an extraction means located proximal to the base and shaped so as to connect to an extraction device.

6. The chisel of claim 1 wherein the distal portion of the base comprises upper, intermediate and lower portions, each having a width, wherein at least a distal portion of each of the upper, intermediate and lower portions has a substantially equal width, so that the distal end of the base comprises a substantially blocky portion.

7. The chisel of claim 1 wherein the base is shaped so as to provide debris pathways.

8. The chisel of claim 1 wherein the base further comprises an intermediate portions having a width, and wherein the intermediate portion width is thinner than the upper and lower portion widths, thereby providing flutes for removal of the debris.

9. The chisel of claim 8 wherein the intermediate portion of the base narrows at the distal end thereof to form at least one secondary orthogonal shaver.

10. The chisel of claim 9 wherein the guide includes a neck extending distally from the intermediate portion of the base, and wherein the at least one secondary orthogonal shaver is located on either side of and proximal to the neck.

11. The chisel of claim 1 wherein the base further comprises an intermediate portions wherein the upper and lower portions of the base do not contact at least a portion of the intermediate portion, so that debris pathways are formed therebetween.

12. The chisel of claim 11 wherein the intermediate portion comprises lateral portions, and the upper and lower portions are integrally connected to the lateral intermediate portions.

13. The chisel of claim 1 wherein the base has an integral I-beam-like shape and further comprises an intermediate portion, wherein the upper base portion integrally connected to the intermediate portion, and the lower base portion, integrally connected to the intermediate portion,
wherein each of the intermediate, upper and lower portions has a width, and
wherein the width of each of the upper and lower portions is greater than the width of the intermediate extending portion.

14. The chisel of claim 13 wherein the I-beam-like shape is an I-beam shape.

15. The chisel of claim 13 wherein the I-beam-like shape is a bulging I-beam shape.

16. The chisel of claim 13 wherein the I-beam-like shape is a bow-tie shape.

17. The chisel of claim 13 wherein the guide includes a neck portion extending distally from the intermediate portion and a head portion extending distally from the neck.

18. The chisel of claim 17 wherein the neck is rectangularly shaped.

19. The chisel of claim 17 wherein the neck widens at an angle $\beta$ as it extends distally.

20. The chisel of claim 19 wherein the upper shaving portion comprises an outer surface and an inner surface whose intersection forms a tip having an angle $\alpha$ suitable for shaving endplates, and wherein the angle $\beta$ is substantially equal to the angle $\alpha$.

21. The chisel of claim 17 wherein the head has a tapered distal portion which narrows distally.

22. The chisel of claim 21 wherein the taper distal portion of the head portion forms an angle $\gamma$ of between 30 and 60 degrees.

23. The chisel of claim 17 wherein the head portion has an axial cross section having a bullet shape.

24. The chisel of claim 17 wherein the head portion has a nipple-like distal portion.

25. The chisel of claim 17 wherein the head portion has a radial cross-section having a circular shape.

26. The chisel of claim 17 wherein the head portion has an axial cross section having a rectangular shape having a height and a width.

27. The chisel of claim 26 wherein the head portion has a height and a width, and is dimensioned so that the height is at least 5 times the width.

28. The chisel of claim 1 wherein the upper shaving portion comprises an outer surface and an inner surface whose intersection forms a tip having an angle $\alpha$ suitable for shaving endplates.

29. The chisel of claim 28 wherein the angle α is between 20 and 40 degrees.

30. The chisel of claim 28 wherein the lower shaving portion comprises an outer surface and an inner surface whose intersection forms a tip having the same angle α as that of the upper shaving portion.

31. The chisel of claim 1 wherein the guide comprises a neck portion extending distally from the base and a head portion extending from the neck, wherein the head comprises upper and lower lands.

32. The chisel of claim 31 wherein at least a portion of each land extends further distally than the shaving portions.

33. The chisel of claim 1 wherein the guide is substantially centered between the shaving portions.

34. The chisel of claim 1 wherein the guide and the upper shaving portion each have a width, and the width of the guide is no more than 50% of the shaving portion width.

35. The chisel of claim 1 wherein the guide width is no more than 25% of the shaving portion width.

36. The chisel of claim 1 wherein the guide comprises a neck portion extending from the base and a head portion extending from the neck, and the head is sufficiently thin and centered so that the entire guide width is located within the middle one-third of the width of the shaving portions.

37. The chisel of claim 36 wherein the guide is located within the middle one-fifth of the width of the shaving portions.

38. A vertebral endplate chisel comprising:
   a) a base having upper, lower and intermediate portions, and proximal and distal portions,
   b) no more than two shaving portions for contouring vertebral endplates, comprising:
      i) an upper shaving portion extending distally from the upper portion, and
      ii) a lower shaving portion extending distally from the lower portion, the upper and lower shaving portions being disposed substantially parallel to each other to define a separation distance, and
   c) a guide extending from the intermediate portion of the base and forming a head portion, wherein the head portion of the guide extends further distally than the shaving portions,
wherein the guide is a non-cutting centering device adapted to center the chisel within the disc space so that equal amounts of bone are removed from each endplate by the shaving portions as the chisel moves through the disc space.

39. The chisel of claim 38 wherein each shaving portion comprises a vertically extending portion extending toward the opposite shaving portion for a distance of up to 30% of the separation distance.

40. The chisel of claim 38 wherein each shaving portion has substantially no vertically extending portion.

41. A vertebral endplate chisel comprising:
   a) a base having upper and lower portions, and proximal and distal portions,
   b) an upper shaving portion extending distally from the upper portion,
   c) a lower shaving portion extending distally from the lower portion,
   the upper and lower shaving portions being disposed substantially parallel to each other, and
   d) a single guide disposed between the shaving portions and extending distal to the shaving portions, and having a height and a width, wherein the height of the single guide at least 5 times greater than its width,
wherein the guide is a non-cutting centering device adapted to center the chisel within the disc space so that equal amounts of bone are removed from each endplate by the shaving portions as the chisel moves through the disc space.

42. A vertebral endplate chisel comprising:
   a) a base having upper and lower portions extending distally therefrom,
   b) an upper shaving portion extending distally from the upper portion,
   c) a lower shaving portion extending distally from the lower portion, the upper and lower shaving portions being disposed substantially parallel to each other, and
   d) a single guide disposed between the shaving portions and extending distal to the shaving portions, and having a height and a width, wherein the width of the single guide no more than 50% of the width of the upper and lower shaving portion.
wherein the guide is a non-cutting centering device adapted to center the chisel within the disc space so that equal amounts of bone are removed from each endplate by the shaving portions as the chisel moves through the disc space.

* * * * *